United States Patent [19]

Lopez

[11] Patent Number: 5,374,248

[45] Date of Patent: Dec. 20, 1994

[54] INFUSION MANIFOLD

[75] Inventor: Georges A. Lopez, Craponne, France

[73] Assignee: Cair L.G.L., Tarare, France

[21] Appl. No.: 997,030

[22] Filed: Dec. 28, 1992

[30] Foreign Application Priority Data

Dec. 27, 1991 [FR] France ................ 91 16451

[51] Int. Cl.⁵ .......................................... A61M 37/00
[52] U.S. Cl. ..................................... 604/82; 604/80;
604/905; 604/246; 137/382
[58] Field of Search ............................ 604/57-60,
604/80-89, 124, 130-133, 169, 173, 905, 90,
65-67, 49, 91, 246, 247, 30, 191, 410, 258, 151,
32; 128/762, 764, 766; 222/145, 330, 132, 136;
137/382, 343, 377

[56] References Cited

U.S. PATENT DOCUMENTS

| | | | |
|---|---|---|---|
| 4,655,762 | 4/1987 | Rogers | 604/403 |
| 4,804,012 | 2/1989 | Goldman et al. | 137/343 |
| 5,074,334 | 12/1991 | Onodera | 137/625.41 |
| 5,193,574 | 3/1993 | Lopez | 137/382 |
| 5,217,432 | 6/1993 | Rudzena et al. | 604/80 |

FOREIGN PATENT DOCUMENTS 2617717 1/1989 France.

*Primary Examiner*—John D. Yasko
*Assistant Examiner*—V. Alexander
*Attorney, Agent, or Firm*—Oliff & Berridge

[57] ABSTRACT

A manifold has a plurality of stopcocks wrapped in a flexible cellular material saturated with an antiseptic liquid and contained in a housing. Each control element of the stopcocks is removable and can be rotationally integrated with a head portion of a stopcock via a shaped male part. The shaped male part engages a female cavity of a matching shape through openings provided in the housing and in the cellular material opposite the stopcocks. Markings showing the position of the stopcocks are visible from the exterior of the housing when the element is withdrawn.

11 Claims, 2 Drawing Sheets

INFUSION MANIFOLD

BACKGROUND OF THE INVENTION

The present invention relates to an infusion manifold.

A manifold of this kind is used when a patient must receive via infusion, simultaneously or not, several products of different kinds. It includes a number of stopcocks, generally three or four, each of which is connected to a reservoir containing one of the products to be infused and, either directly or through other stopcocks, to a tube to feed the products to the patient.

This type of manifold must be carefully protected against any microbial contamination and must permit frequent operation of the stopcocks, with every guarantee of safety as regards operation and positioning of the stopcocks.

To achieve these contradictory goals, it is known that manifolds can be wrapped in a flexible cellular material saturated with antiseptic liquid and then placed in a housing that can be opened to allow access to the stopcocks. The housing comprises an apparatus for fastening it heightwise to a support or bracket.

It is readily apparent that the need to open the housing and operate the stopcocks affects the sterility of the manifold. In addition, existing manifolds do not permit checking the positions of the plugs of the several stopcocks without opening the housing. Finally, the fact that the upper part of the cellular material must be pulled back to reveal the control elements of the stopcocks causes the nurse or patient to stain their fingers, since the antiseptic liquids used are generally colored.

It is also known from French Patent 2,617,717 to provide an infusion manifold of this type in which the stopcocks have control elements that project outside the housing, the control elements being permanently mounted on the stopcocks or on the upper shell of the housing.

The shape of the control elements, with three perpendicular arms, makes it immediately apparent in what position the stopcock is located, each arm being located parallel to one of the passageways in the stopcock.

This arrangement ensures good protection of the manifold against germs, but has the disadvantage of permitting undesired operation or unauthorized manipulation of the stopcocks, which can have harmful consequences for the patient.

SUMMARY OF THE INVENTION

A goal of the present invention is to overcome all of these disadvantages.

The manifold in question is of the type comprising a plurality of stopcocks wrapped in a flexible cellular material saturated with an antiseptic liquid, contained in a housing.

According to the invention, each control element of the stopcocks is removable and can be rotationally integrated with the head of the plug of a stopcock via a shaped male part. The part can be fitted through openings made in the housing and in the cellular material opposite the plug of each stopcock, into a female cavity of corresponding shape. The apparatus includes an arrangement for indicating the position of the plug, visible from the outside of the housing when the control element is withdrawn.

Thus, in the manifold according to the invention, the stopcock control elements are located outside the housing so that the plugs of the stopcocks can be operated without it being necessary to open the housing and handle the cellular material. The manifold thus remains perfectly sterile and protected against the growth of germs. The removability of the control elements prevents any improper manipulation of the stopcocks.

Moreover, the indicating arrangement that is part of the manifold is visible from the outside of the housing and immediately provides information on the positions of the plugs without it being necessary to open the housing.

BRIEF DESCRIPTION OF THE DRAWINGS

The invention will be clearly understood from the following description which refers to the attached schematic diagram showing as a nonlimiting example one preferred embodiment of the infusion manifold in question.

DETAILED DESCRIPTION OF PREFERRED EMBODIMENTS

Preferably, the indicating arrangement for each stopcock consists of a ring engaged in the opening in the housing opposite the stopcock and which is pivotably mounted relative to the housing, the opening having a shape matching that of the shaped male part of the removable control element in order to be able to be rotationally integrated with the control element. The ring has at least one marking indicating the position of the plug, and the housing has markings located to correspond to the different possible positions of the plugs.

The control element of each stopcock can therefore pivot the ring at the same time as the plug, and the positions of the reference marking(s) of the ring relative to the markings on the housing make it possible to see the positions of the plugs perfectly from the outside of the housing and after withdrawing the control elements.

Advantageously, the opening in the ring has a shape having at least one end of a distinct nature (such as an arrow) constituting the marking(s) indicating the position(s) of the stopcocks. Thus, in the case of three-way stopcocks, the opening in the ring and hence consequently the cross section of the female cavity in the plug and the corresponding male part of the control element can have a triangular shape, with each angle of the triangle corresponding to one of the passageways in the stopcock.

According to a first embodiment of the invention, the shaped male part of the control element passes through the opening in the ring and engages a female cavity provided in the stopcock.

According to a second embodiment of the invention, which has the advantage over the previous embodiment of guaranteeing still better the asepsis of the manifold for each stopcock, the ring has an axial extension that projects into the interior of the housing. The extension closes the opening in the ring and has a male shape matching a female cavity made in the stopcock, into which it fits. Therefore there is no direct contact between the stopcock and the control element and hence no risk of contamination.

Figure 1:
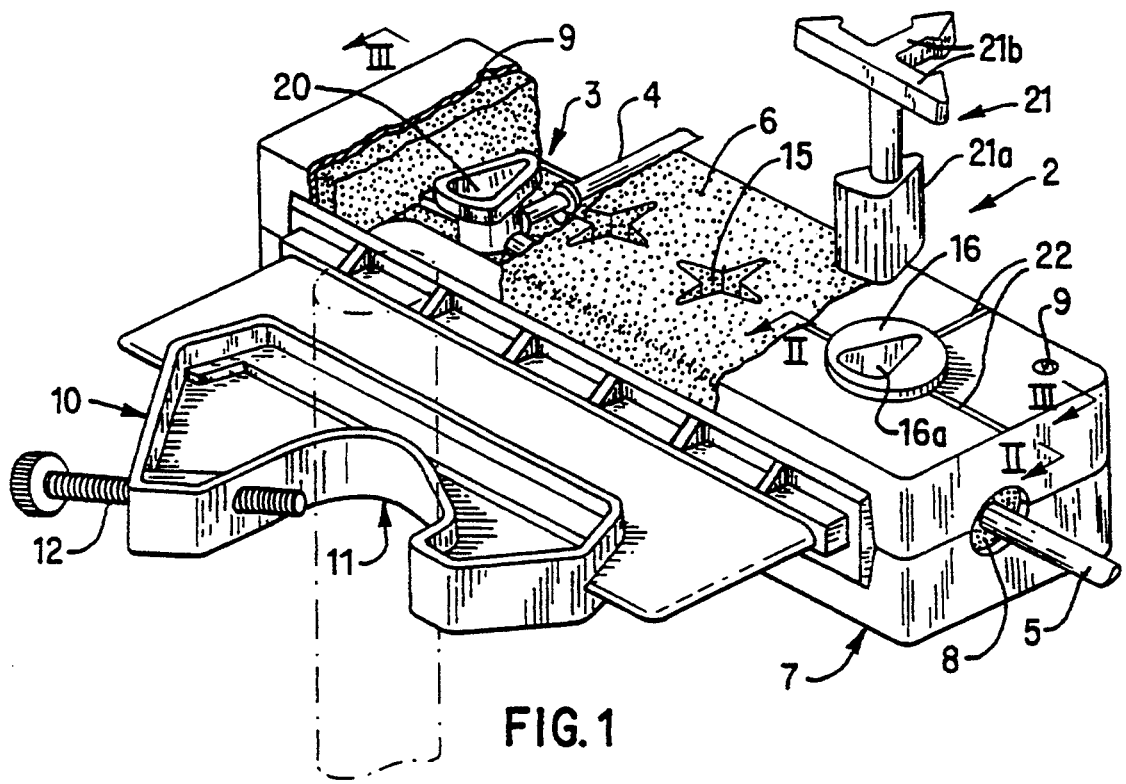
FIG. 1 is a perspective view, partially cut away.
Figure 3:
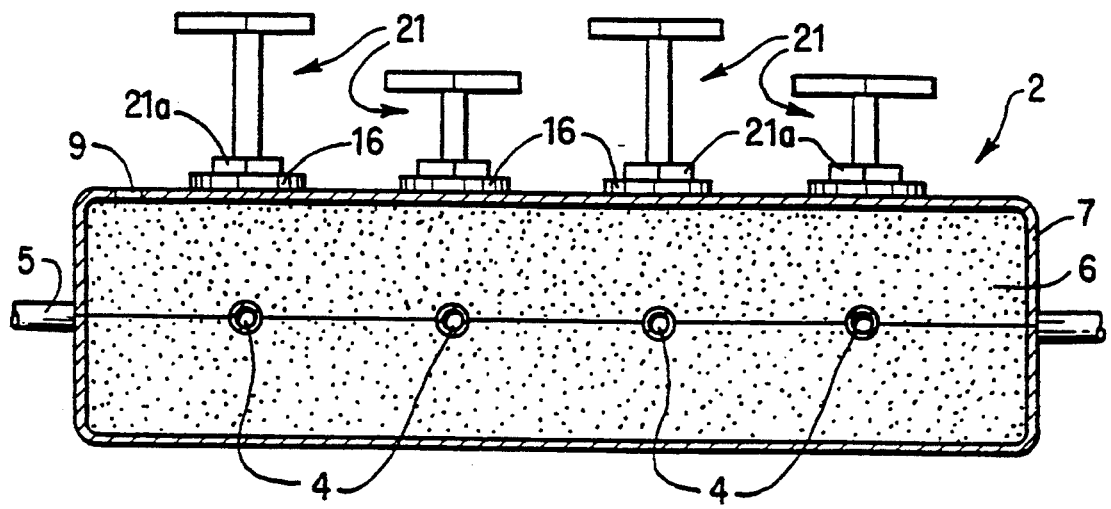
FIG. 3 is a longitudinal section along line III—III in FIG. 1.

FIGS. 1 and 3 show from different angles an infusion manifold 2 having a plurality of stopcocks 3, one of which is visible in FIG. 1. Each stopcock 3 is connected through a tube 4 to a reservoir (not shown) containing one of the products to be infused and, directly or through other stopcocks 3, to a tube 5 for feeding the products to be infused to the patient. Stopcocks 3, as well as the ends of tubes 4 and 5, are wrapped in flexible cellular material 6 saturated with an antiseptic liquid, and are contained in a housing 7. Housing 7 is pierced by holes 8 to allow passage of tubes 4 and 5 and holes 9 for introducing the antiseptic liquid. It also has a plate 10 for attachment heightwise, having a concave part 11 designed to be fitted around a support or a bracket, and a screw 12 for locking said support or said bracket to said concave part 11.

As shown in FIG. 1, housing 7 and cellular material 6 have openings opposite the plug of each stopcock 3. Openings 15 provided in cellular material 6 are composed of two intersecting slots. The openings made in housing 7 have a circular cross section and each receives a ring 16 that can pivot relative to housing 7.

FIG. 1 also shows that the head of the plug of each stopcock 3 has a female cavity 20 with an essentially triangular shape. Opening 16a of each ring 16 has a shape identical to that of female cavity 20 and each control element 21 of each stopcock 3 is removable and has a male part 21a having a shape matching those of cavity 20 and opening 16a.

It must be specified that stopcocks 3 are of the three-way variety and that each angle of the triangle that delimits opening 16a corresponds to one of the openings in the stopcock.

In addition, the upper surface of housing 7 with openings opposite each stopcock 3, has markings 22 imprinted or engraved on it, corresponding to the various possible positions of the stopcocks.

Figure 2:
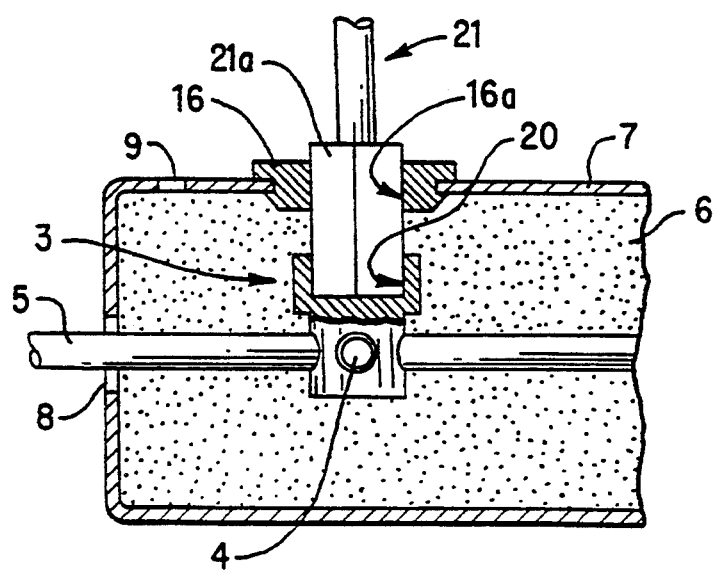
FIG. 2 is a cross section along line II—II in FIG. 1.

It is clear from FIG. 2 that shaped male part 21a of control element 21 is designed to be fitted through opening 16a of ring 16 and then into cavity 20 in the head of the plug of stopcock 3. The rotary connection obtained between control element 21 and the plug allows stopcock 3 to be manipulated. Since control element 21 is located on the outside of housing 7, the plugs of stopcocks 3 can be operated without it being necessary to open housing 7 and to handle cellular material 6. Manifold 2 thus remains perfectly sterile. The removability of control elements 21 also prevents improper manipulation, in other words manipulation of stopcocks 3 that is not desired or is unauthorized.

The rotary connection between control element 21 and ring 16 makes it possible to pivot said ring 16 at the same time as the stopcock and to align with markings 22 the markings showing the position of the plug that form the angles of the triangle that delimits its opening 16a. It is therefore possible to determine immediately the positions of the stopcocks from the outside of housing 7 without having to open the housing.

Of course cavity 20, male part 21a, and opening 16a may have different shapes. The marking of the plug position can thus be provided simply by means of perpendicular arms 21b of control element 21. However this implies fitting the control element through opening 16a in order to be able to make this determination.

FIG. 3 shows more specifically that control elements 21 can be of different lengths in order to facilitate their manipulation.

Figure 4:
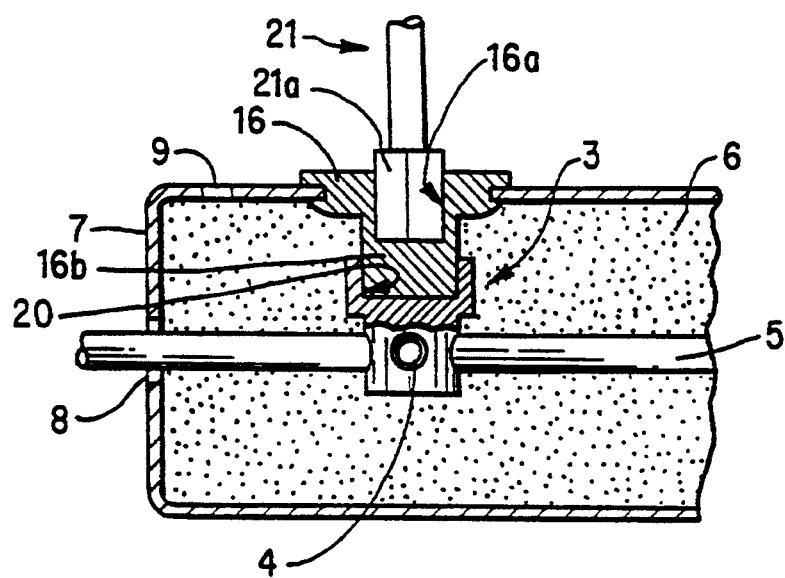
FIG. 4 is a section similar to FIG. 2 in a second embodiment.

FIG. 4 on the other hand shows an embodiment of the invention that has the advantage over that shown in FIG. 2 of providing a better guarantee of the asepsis of manifold 2. At each stopcock 3, ring 16 has an axial projection 16b projecting into the interior of housing 7, said extension 16b closing opening 16a of ring 16 and having a male shape matching female cavity 20 in the stopcock. This shape 16b is designed to be fitted into cavity 20. Thus there is no direct contact between the plug and control element 21 and hence no risk of contamination.

Although the invention has been described in detail with reference to preferred embodiments thereof, the description is intended to be illustrative, not limiting. Various modifications may be made without departing from the spirit and scope of the invention as defined in the appended claims.

What is claimed is:

1. An infusion manifold having a plurality of stopcocks wrapped in a flexible cellular material saturated with an antiseptic liquid and contained in a housing, each of said stopcocks being controlled by a control element, said control element being removable and having a shaped male part, said male part engagable with a corresponding female cavity in a head portion of said stopcocks through openings in said housing and said cellular material opposite the head portion of said stopcocks, the manifold further comprising marking means for marking positions of the stopcocks, said marking means being visible from the outside of said housing when said control element is withdrawn.

2. An infusion manifold according to claim 1, wherein the marking means comprises a ring engaged in the opening in said housing opposite each of said stopcocks and pivotably mounted relative to said housing, said ring having an opening which has a shape matching that of said shaped male part such that said ring is rotationally integratable with said control element, said ring comprising at least one marking indicating the position of the stopcocks, said marking means further comprising markings on said housing corresponding to the positions of the stopcocks.

3. An infusion manifold according to claim 2, wherein said opening of said ring is shaped such that at least one end is of a distinct nature constituting the marking indicating the positions of the stopcocks.

4. An infusion manifold according to claim 3, wherein said opening of said ring has a triangular shape, each point of the triangle corresponding to one of the positions of the stopcocks.

5. An infusion manifold according to claim 2, wherein said shaped male part of said control element is extendible through said opening of said ring to engage said female cavity in the head portion of said stopcocks.

6. An infusion manifold according to claim 2, wherein said ring comprises an axial extension projecting into said housing, said extension having a male shape matching said female cavity in the head portion of said stopcocks and extending into said cavity.

7. A infusion manifold according to claim 2, wherein said markings on said housing are imprinted on said housing.

8. A infusion manifold according to claim 2, wherein said markings on said housing are engraved on said housing.

9. An infusion manifold according to claim 1, further comprising openings provided in an upper surface of said housing.

10. An infusion manifold according to claim 1, wherein said control elements comprise shafts of different lengths.

11. An infusion manifold according to claim 1, wherein each of said stopcocks are controlled by a respective control element and further comprising a plate for attachment to a support member, said plate having a concave part designed to be fitted around said support member and a screw for locking said concave part to said support member.

* * * * *